(12) United States Patent
Abbruscato

(10) Patent No.: US 8,320,576 B1
(45) Date of Patent: Nov. 27, 2012

(54) PIEZO ELEMENT STETHOSCOPE

(76) Inventor: Charles Richard Abbruscato, Viera, FL (US)

(*) Notice: Subject to any disclaimer, the term of this patent is extended or adjusted under 35 U.S.C. 154(b) by 539 days.

(21) Appl. No.: 12/590,362

(22) Filed: Nov. 6, 2009

(51) Int. Cl.
A61B 7/04 (2006.01)

(52) U.S. Cl. .................... 381/67; 600/586; 600/528

(58) Field of Classification Search .......... 381/67, 381/71.5, 190; 600/498, 586, 528
See application file for complete search history.

(56) References Cited

U.S. PATENT DOCUMENTS

| | | |
|---|---|---|
| 4,535,205 A | 8/1985 | Ravinet et al. |
| 4,784,154 A | 11/1988 | Shirley et al. |
| 5,022,405 A | 6/1991 | Hok et al. |
| 5,131,400 A | 7/1992 | Harada et al. |
| 5,195,142 A | 3/1993 | D'Avolio et al. |
| 5,238,000 A | 8/1993 | Niwa |
| 5,283,835 A | 2/1994 | Athanas |
| 5,284,150 A | 2/1994 | Butterfield et al. |
| 5,467,771 A | 11/1995 | Narimatsu et al. |
| 5,551,437 A | 9/1996 | Lotscher |
| 5,908,027 A | 6/1999 | Butterfield et al. |
| 5,932,849 A | 8/1999 | Dieken |
| 6,002,777 A | 12/1999 | Grasfield et al. |
| 6,159,166 A | 12/2000 | Chesney et al. |
| 6,478,744 B2 * | 11/2002 | Mohler ............... 600/485 |
| 6,491,647 B1 | 12/2002 | Bridger et al. |
| 6,498,854 B1 | 12/2002 | Smith |
| 6,661,897 B2 | 12/2003 | Smith |
| 6,937,736 B2 | 8/2005 | Toda |
| 2001/0014162 A1 * | 8/2001 | Orten ................ 381/67 |
| 2005/0058298 A1 | 3/2005 | Smith |
| 2005/0157888 A1 | 7/2005 | Yang |
| 2007/0106179 A1 | 5/2007 | Bagha et al. |
| 2007/0165872 A1 * | 7/2007 | Bridger et al. ........... 381/67 |
| 2008/0257637 A1 * | 10/2008 | Miller et al. ........... 181/131 |
| 2011/0197921 A1 * | 8/2011 | Rubin et al. ........... 134/18 |

* cited by examiner

*Primary Examiner* — Vivian Chin
*Assistant Examiner* — Friedrich W Fahnert
(74) *Attorney, Agent, or Firm* — Miller Patent Services; Jerry A. Miller

(57) ABSTRACT

A passive stethoscope chest piece has a chest piece housing containing a passive piezoelectric (piezo) element mounted within a metal housing. The piezo element converts body signals to an electrical representation. A pair of electrical connections attached to the metal plate and the piezoelectric layer of the piezo element pass the electrical representation outside the housing for processing by external circuitry. This abstract is not to be considered limiting, since other embodiments may deviate from the features described in this abstract.

20 Claims, 1 Drawing Sheet

PIEZO ELEMENT STETHOSCOPE

COPYRIGHT AND TRADEMARK NOTICE

A portion of the disclosure of this patent document contains material which is subject to copyright protection. The copyright owner has no objection to the facsimile reproduction of the patent document or the patent disclosure, as it appears in the Patent and Trademark Office patent file or records, but otherwise reserves all copyright rights whatsoever. Trademarks are the property of their respective owners.

BACKGROUND

Traditional stethoscopes pick up signals generated within the body with a chest piece head and deliver them as an acoustic signal to an ear piece via a tube for the clinician to hear. The most common type of electronic stethoscopes use a chest piece head to convert the body's sounds to acoustic, then use microphones to convert the acoustic signal to an analog electrical signal. The analog electrical signal can be processed with analog filters and amplifiers or converted to digital format and processed with digital signal processing techniques.

Another type of electronic stethoscopes uses a piezo (piezoelectric) element to directly convert the internal body signals to analog electrical signals. But using piezo elements creates new challenges. Electronically, a piezo element is modeled as a low impedance voltage source in series with a capacitance. The piezo elements currently in use have a very small equivalent capacitance. This is an important consideration when coupling the piezo element to an amplifier to boost the signal so that it can be heard by the clinician. Unless the amplifier accounts for and compensates for the effects of the series capacitance, the frequency response of the body signal can be altered.

In practice, the capacitance of a coupling cable is significant enough in relation to the capacitance of the piezo element, that it adversely affects the frequency response of the body signal. To avoid the distortions to the signal this could cause, the current state of the art is to put an electronic buffer amplifier in the same housing as the piezo element. The input capacitance of the buffer amplifier is very low and its input impedance is very high, thus preserving the fidelity of the signal from the piezo element. The output impedance of the buffer amplifier is low and relatively immune to the characteristics of the load, including the capacitance and inductance of a filter or cable. The current state of the art for electronic stethoscopes using piezo elements for the pickup sensor requires that a buffer amplifier be co-located in the same housing with the piezo element.

However, by housing the buffer amplifier and the piezo element together, sanitizing the chest piece assembly becomes problematic. Unless the housing assembly is sealed against moisture and liquids, the buffer amplifier electronic components could become damaged while in an autoclave or other liquid sanitizing cleaning method. Sealing the housing with the piezo element and buffer amplifier such that the sensor operation of the piezo element is not adversely affected is difficult and expensive. Therefore, to be competitive in the market, the housing is not perfectly sealed. As a result, these piezo element based electronic stethoscopes are not used in a surgical environment where sanitizing or sterilizing is required.

BRIEF DESCRIPTION OF THE DRAWINGS

Certain illustrative embodiments illustrating organization and method of operation, together with objects and advantages may be best understood by reference detailed description that follows taken in conjunction with the accompanying drawings in which.

DETAILED DESCRIPTION

Figure 1:
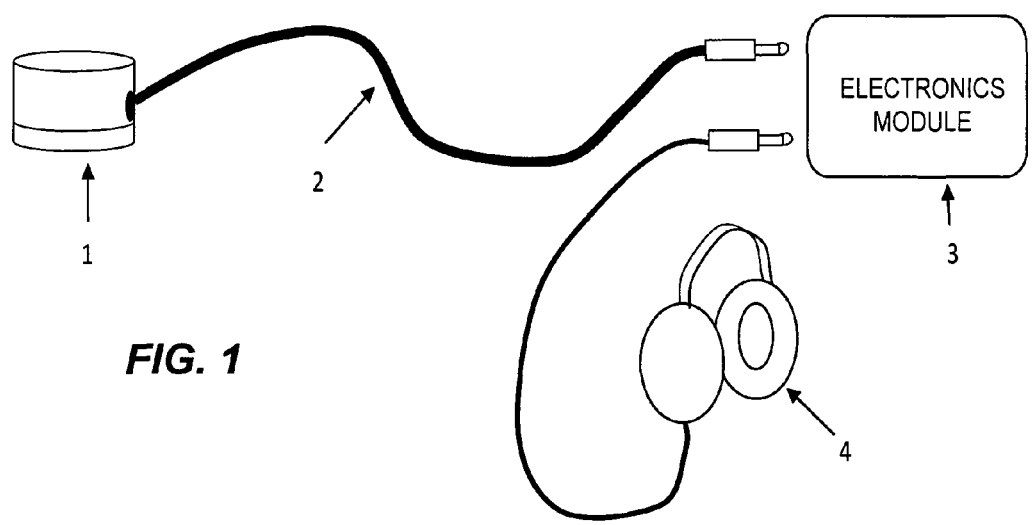
FIG. 1 is an example of a complete stethoscope system consistent with certain embodiments of the present invention.

While this invention is susceptible of embodiment in many different forms, there is shown in the drawings and will herein be described in detail specific embodiments, with the understanding that the present disclosure of such embodiments is to be considered as an example of the principles and not intended to limit the invention to the specific embodiments shown and described. In the description below, like reference numerals are used to describe the same, similar or corresponding parts in the several views of the drawings.

The terms "a" or "an", as used herein, are defined as one or more than one. The term "plurality", as used herein, is defined as two or more than two. The term "another", as used herein, is defined as at least a second or more. The terms "including" and/or "having", as used herein, are defined as comprising (i.e., open language). The term "coupled", as used herein, is defined as connected, although not necessarily directly, and not necessarily mechanically.

Reference throughout this document to "one embodiment", "certain embodiments", "an embodiment", "an example", "an implementation" or similar terms means that a particular feature, structure, or characteristic described in connection with the embodiment, example or implementation is included in at least one embodiment, example or implementation of the present invention. Thus, the appearances of such phrases or in various places throughout this specification are not necessarily all referring to the same embodiment, example or implementation. Furthermore, the particular features, structures, or characteristics may be combined in any suitable manner in one or more embodiments, examples or implementations without limitation.

The term "or" as used herein is to be interpreted as an inclusive or meaning any one or any combination. Therefore, "A, B or C" means "any of the following: A; B; C; A and B; A and C; B and C; A, B and C". An exception to this definition will occur only when a combination of elements, functions, steps or acts are in some way inherently mutually exclusive.

A stethoscope utilizing a piezo element in a manner consistent with embodiments of the present invention places the piezo element for the chest piece sensor in a simple housing with novel features. A low cost, rugged, passive piezo element is used as the pickup sensor such that no electronics are used in the chest piece. This allows it to be cleaned in a steam autoclave or other sanitizing or sterilizing method without risk of damaging the chest piece.

In certain example embodiments, the piezo element is a metal, such as brass or stainless steel. The housing comes in two pieces—a Top Piece and Bottom Piece. The Top Piece is metal, preferably stainless steel, and clamps the piezo element around its rim against the Bottom Piece The Top Piece has a special internal protrusion to serve as a stop behind the piezo element to prevent it from over flexing, thus making it very rugged.

The Top Piece of the chest piece is made from a non-corroding metal such as stainless steel, which is not damaged or degraded in an autoclave or other sanitizing or sterilizing method. In addition, the metal housing provides a weight or mass that works against the piezo element to improve the performance of the piezo element and reduce extraneous pickup of noise from the user holding the chest piece.

In accord with certain implementations, a low cost piezo based chest piece need not contain active electronic elements and batteries and requires no external power source to function. The chest piece head has features to make it rugged and has significant mass to improve performance. The chest piece is detachable from the electronic stethoscope and can be sanitized or sterilized separate from the electronics module, thus allowing its use in a surgical environment.

FIG. 1 shows the complete stethoscope system with the chest piece 1, the coupling cable 2, the electronics module 3, and the headset 4. The chest piece 1 senses the body signals and converts them to electrical analog signals, which are sent over the cable to the electronics module 3. Electronics module 3 amplifies the signal and may carry out other signal processing functions. Many variations on this can be devised. For example, the cable 2 can be attached to the chest piece 1 or plug into the chest piece 1 at one end and plug into the electronics module 3 at the other end. Other audio or visual signal processing and/or reproduction can be used in place of headphones 4. Either way, the chest piece 1 can preferably be removed and sanitized or sterilized separately from the electronics module.

The electronics module 3 contains the amplifiers and filters and other components to provide the audible signal representing the body sounds to the clinician listening on the headset. The listening means can be a headset, an ear bud type listening device, loudspeaker or any convenient means of listening to the audio signal. Other implementations may also record or provide a visual display of the signal from the chest piece 1.

Figure 2:
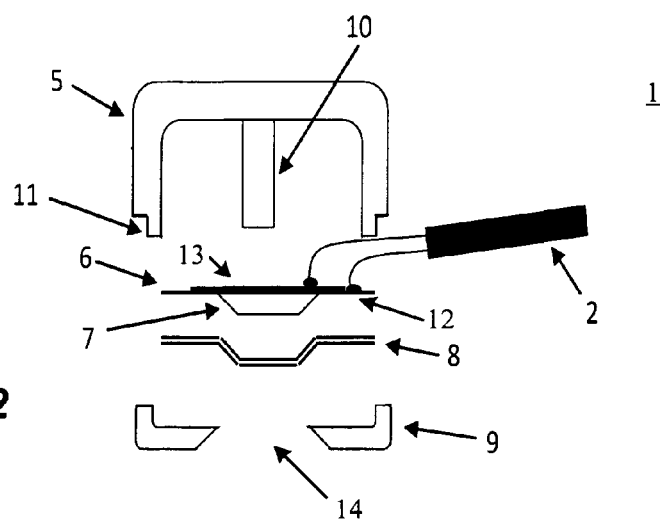
FIG. 2 is a diagram depicting an example of a chest piece implementation for a stethoscope consistent with certain embodiments of the present invention.

FIG. 2 shows the construction of an example implementation of the chest piece 1 in cross section. The core of the chest piece 1 is a piezoelectric element sensor 6 with a suitable structure to hold the piezo element sensor 6 in place and a set of wires 2 attached to the two electrical contacts of the piezo sensor 6 to convey the signals that it picks up. The piezo sensor element 6 may be made up of a round metal plate 12, for example brass or stainless steel, with a ceramic (or other piezoelectric material) disk 13 of smaller diameter than the metal plate 12 attached to one side. The signal generated by the piezo element 6 is a voltage potential between the ceramic disk 13 and the metal plate 12 as a result of the piezoelectric effect. While a disk shape is preferred and used as an illustrative example herein, the ceramic or other piezoelectric layer can be of any suitable geometry (square, oval, rectangular, etc).

The bottom piece 9 of the chest piece 1 has a hole 14 in the middle of its bottom face. The piezo element 6 has a plastic or rubber button 7 adhered to its metal plate 12 side and two wires in a cable 2 attached (typically soldered or welded) to the top side where the ceramic disk 13—one wire to the ceramic element 13 and one wire to the metal plate 12. The piezo element 6 is placed inside the bottom piece 9 so that the button 7 protrudes into the opening in the face of the bottom piece 9. Pressure signals on the button 7 are conveyed to the piezo element 6 and converted to electrical signals that are in turn conveyed via the wires of cable 2. A Silicone cover 8 is placed over the piezo element 6 with button 7 attached to provide an inert material for the surface that would touch the patient. The top piece 5 has its bottom rim 11 shaped so that it fits inside the bottom piece and clamps down on the outside rim of the piezo element 6 to the bottom piece 9. A hole or slot is cut in the top piece 5 for the cable 2 to pass through.

Using a metal top piece 5 to clamp the outside rim of the piezo element 6 firmly against the bottom piece 9 maximizes the performance of the piezo element 6. The relatively heavy mass of the metal top piece 5 inhibits the vibration from the piezo element 6 from being dissipated by the metal shell comprised of the top piece 5 and the bottom piece 9 and channels the maximum vibration to the ceramic disk 13 of the piezo element 6, thus generating the maximum signal. The top piece 5 is designed to have relatively high mass of about 12 grams to inhibit vibration. A top piece 5 mass of about 9-20 grams is currently preferred.

There is a post or protrusion 10 inside the top piece 5 that extends nearly to the piezo element 6. The post or protrusion 10 provides a backstop for the piezo element 6 so that it cannot flex excessively and be damaged. Without post or protrusion 10, the piezo element 6 could be damaged by pressing hard on the button 7. The post or protrusion 10 serves as a "backstop" and can be secured to top piece 5 or could be molded to be an integral part of top piece 5. In one preferred implementation, the protrusion 10 rests approximately 0.6 mm from the top of the ceramic disk 13 of the piezo element 6 when fully assembled in order to limit the excursion of the piezo element. The exact distance or range of distance is somewhat dependent upon the actual piezo element 6 used. The distance can be smaller up to the point where the ceramic disk 13 nearly touches the protrusion 10. The distance can be larger but if it gets too large for a selected piezo element 6, then the protrusion 10 would not prevent damage to the piezo element 6. Hence, the protrusion 10 should be spaced far enough away from the piezo element 6 so as not to interfere with the movement of the piezo element 6, but should be close enough to stop its movement beyond a point where the piezo element 6 would incur damage from further movement. For piezo elements of the size used herein, a gap of approximately 0.5-0.7 mm is suitable and preferably about 0.6 mm.

The piezo element with a metal plate has a relatively large series capacitance and is capable of generating a relatively large analog electrical signal with the chest piece assembly 1 described. By selecting a piezo element with a series capacitance that is a at least 1-2 orders of magnitude greater than the distributed capacitance of a connecting cable plus the input capacitance of the buffer amplifier, the buffer amplifier module 3 can be implemented separately connected by an inexpensive audio cable without introducing discernible distortion and noise. For one simple inexpensive implementation with a satisfactorily large capacitance, the piezo element 6 is approximately 0.23 mm thick and approximately 27 mm in diameter resulting in over 570 $mm^2$ of surface area and a series capacitance of the piezo element 6 of between 10,000 pF-40,000 pF. The distributed capacitance of the cable 3, which may be an inexpensive 2 meter audio cable (unbalanced audio cable typically has a capacitance of 200 pf per meter), plus the amplifier input capacitance (typically in the range of 30 pF) is approximately 430 pF resulting in no discernable distortion in the presently preferred implementation. The buffer amplifier is constructed using a conventional commercially available operational amplifier, and the cable 3 is a two conductor shielded audio cable approximately 2-3 meters long. All the elements in the chest piece, when constructed as described, can be sanitized in an autoclave or liquid sanitizing solution without damage. Many variations will occur to those skilled in the art.

Hence, a stethoscope chest piece consistent with certain implementations uses a piezo element as the sensor to pick up body sounds, where the piezo element is passive, is made from an inert or stable metal, there are no active electronic components in the chest piece, all components of the chest piece are inert or stable such that they are not damaged if they are sanitized in an autoclave or liquid sanitizing solution and no special sealing is required to prevent damage if the chest piece is sanitized in an autoclave or liquid sanitizing solution.

Certain implementations use a piezo element that is relatively large (e.g. about 27 mm in diameter) and thereby yields a relatively large equivalent capacitance (e.g. 10,000 pF-40,000 pF) so that the output of the piezo element can be coupled to an external amplifier module with an ordinary inexpensive audio cable. The chest piece enclosure material that is not only inert or stable, but is relatively heavy to maximize the performance of the piezo element and minimize extraneous noise due to handling the chest piece is preferred. A post or protrusion is provided inside the metal chest piece top to provide a backstop to the piezo element to prevent it from being damaged by over flexing.

Combining the above concepts yields a chest piece with high performance, high fidelity, and is easier and less expensive to manufacture than the current state of the art stethoscope implementations incorporating piezo elements.

Thus, in certain implementations, a passive stethoscope chest piece has a chest piece housing containing: a passive piezoelectric (piezo) element having a piezoelectric layer (such as a ceramic disk) and a metal layer (preferably a disk); a pair of electrical connections to the piezo element so that the piezo element serves to pick up body sounds and provide an electrical representation of the body sounds to the electrical connections and pass the electrical representation outside the housing for processing by external circuitry; and wherein the housing includes a backstop comprising a post affixed to the housing and protruding toward a central area of the piezo element.

In certain implementations, no active electronic components are disposed within the housing. In certain implementations, the housing and metal plate are made from an inert or stable metal that can be sanitized in an autoclave or liquid sanitizing solution without degradation of operation. In certain implementations, the housing is unsealed. In certain implementations, the piezo element has approximately 570 mm squared of surface area. In certain implementations, the piezo element has series capacitance of at least 10,000 pF. In certain implementations, the electrical connectors connect to a cable and an external circuit, and wherein the capacitance of the piezo element is at least ten times the combined capacitance of the cable and external circuit. In certain implementations, the back stop is situated so as to prevent the piezo element from flexing beyond a point that would damage the piezo element. In certain implementations, the back stop is situated approximately 5-7 mm from a center of the piezo element.

Another passive stethoscope chest piece has a chest piece housing containing: a passive piezoelectric (piezo) element; a pair of electrical connections to the piezo element so that the piezo element serves to pick up body sounds and provide an electrical representation of the body sounds to the electrical connections and pass the electrical representation outside the housing for processing by external circuitry; wherein no active electronic components are disposed within the housing; and the housing having a back stop situated so as to prevent the piezo element from flexing beyond a point that would damage the piezo element.

In certain implementations, the housing and metal plate are made from an inert or stable metal that can be sanitized in an autoclave or liquid sanitizing solution without degradation of operation. In certain implementations, the housing is unsealed. In certain implementations, the piezo element is approximately 570 mm square in surface area. In certain implementations, the piezo element has series capacitance of at least 10,000 pF. In certain implementations, the piezo element has a series capacitance of between 10,000 pF and 40,000 pF. In certain implementations, the electrical connectors connect to a cable and an external circuit, and wherein the capacitance of the piezo element is at least ten times the combined capacitance of the cable and external circuit. In certain implementations, the back stop is situated approximately 5-7 mm from a center of the piezo element. In certain implementations, the backstop comprises a post affixed to the housing and protruding toward a central area of the piezo element.

Another passive stethoscope chest piece consistent with certain implementations has an unsealed chest piece housing, where the housing and metal plate are made from an inert or stable metal that can be sanitized in an autoclave or liquid sanitizing solution without degradation of operation, the housing containing. A passive piezoelectric (piezo) element has at least 10,000 pF in series capacitance. A pair of electrical connections to the metal plate and ceramic disk of the piezo element so that the piezo element serves to pick up body sounds and provides an electrical representation of the body sounds to the electrical connections and pass the electrical representation outside the housing for processing by external circuitry, wherein no active electronic components are disposed within the housing. The electrical connectors connect to a cable and an external circuit, and wherein the capacitance of the piezo element is at least ten times the combined capacitance of the cable and external circuit. A post is affixed to the housing and forming a back stop situated approximately 5-7 mm from a central area of the piezo element so as to prevent the piezo element from flexing beyond a point that would damage the piezo element. In certain implementations, the post is integral to a portion of the housing.

While certain illustrative embodiments have been described, it is evident that many alternatives, modifications, permutations and variations will become apparent to those skilled in the art in light of the foregoing description.

What is claimed is:

1. A passive stethoscope chest piece, comprising:
a chest piece housing containing:
a passive piezoelectric (piezo) element with a metal plate;
a pair of electrical connections at the metal plate and a piezoelectric layer of the piezo element so that the piezo element serves to pick up body sounds and provides an electrical representation of the body sounds to the electrical connections and pass the electrical representation outside the housing for processing by external circuitry; and
where the housing includes a backstop comprising a post affixed to the housing and protruding toward a central area of the piezo element with their being a gap between the backstop and the piezo element so that the backstop contacts the piezo element if the piezo element is flexed toward the backstop by a distance equal to the gap.

2. The chest piece according to claim 1, where no active electronic components are disposed within the housing.

3. The chest piece according to claim 1, where the housing and metal plate are made from an inert or stable metal that can be sanitized in an autoclave or liquid sanitizing solution without degradation of operation.

4. The chest piece according to claim 1, where the housing is unsealed.

5. The chest piece according to claim 1, where the piezo element has approximately 570 mm squared of surface area.

6. The chest piece according to claim 1, where the piezo element has series capacitance of at least 10,000 pF.

7. The chest piece according to claim 1, where the electrical connectors connect to a cable and an external circuit, and wherein the capacitance of the piezo element is at least ten times the combined capacitance of the cable and external circuit.

8. The chest piece according to claim 1, where the back stop is situated so as to prevent the piezo element from flexing beyond a point that would damage the piezo element.

9. The chest piece according to claim 1, where the back stop is situated approximately 5-7 mm from a center of the piezo element.

10. A passive stethoscope chest piece, comprising:
a chest piece housing containing:
a passive piezoelectric (piezo) element with a metal plate and a piezoelectric layer;
a pair of electrical connections at the metal plate and ceramic disk of the piezo element so that the piezo element serves to pick up body sounds and provides an electrical representation of the body sounds to the electrical connections and pass the electrical representation outside the housing for processing by external circuitry, where no active electronic components are disposed within the housing; and
the housing having a back stop situated so as to prevent the piezo element from flexing beyond a point that would damage the piezo element, where a gap is provided between the backstop and the piezo element so that the backstop contacts the piezo element if the piezo element is flexed toward the backstop by a distance equal to the gap.

11. The chest piece according to claim 10, where the housing and metal plate are made from an inert or stable metal that can be sanitized in an autoclave or liquid sanitizing solution without degradation of operation.

12. The chest piece according to claim 10, where the housing is unsealed.

13. The chest piece according to claim 10, where the piezo element is approximately 570 mm square in surface area.

14. The chest piece according to claim 10, where the piezo element has series capacitance of at least 10,000 pF.

15. The chest piece according to claim 10, where the piezo element has a series capacitance of between 10,000 pF and 40,000 pF.

16. The chest piece according to claim 10, where the electrical connectors connect to a cable and an external circuit, and wherein the capacitance of the piezo element is at least ten times the combined capacitance of the cable and external circuit.

17. The chest piece according to claim 10, where the back stop is situated approximately 5-7 mm from a center of the piezo element.

18. The chest piece according to claim 10, where the backstop comprises a post affixed to the housing and protruding toward a central area of the piezo element.

19. A passive stethoscope chest piece, comprising:
an unsealed chest piece housing, where the housing and metal plate are made from an inert or stable metal that can be sanitized in an autoclave or liquid sanitizing solution without degradation of operation, the housing containing:
a passive piezoelectric (piezo) element with a ceramic disk and a metal plate having at least 10,000 pF in series capacitance;
a pair of electrical connections at the metal plate and ceramic disk of the piezo element so that the piezo element serves to pick up body sounds and provides an electrical representation of the body sounds to the electrical connections and pass the electrical representation outside the housing for processing by external circuitry, where no active electronic components are disposed within the housing;
where the electrical connectors connect to a cable and an external circuit, and where the capacitance of the piezo element is at least ten times the combined capacitance of the cable and external circuit; and
a post affixed to a top piece of the housing and forming a back stop situated approximately 5-7 mm from a central area of the piezo element so as to prevent the piezo element from flexing beyond a point that would damage the piezo element, with the top piece having a mass between 9 and 20 grams.

20. The chest piece according to claim 19, where the post is integral to a portion of the top piece of the housing.

* * * * *